United States Patent
Cao et al.

(10) Patent No.: US 10,342,963 B2
(45) Date of Patent: Jul. 9, 2019

(54) MICROBLADE ARRAY IMPACT APPLICATOR

(71) Applicant: Alza Corporation, Vacaville, CA (US)

(72) Inventors: Michael T. Cao, Milpitas, CA (US); Richard L. Keenan, Saratoga, CA (US); Joseph C. Trautman, Sunnyvale, CA (US)

(73) Assignee: ALZA CORPORATION, Vacaville, CA (US)

( * ) Notice: Subject to any disclaimer, the term of this patent is extended or adjusted under 35 U.S.C. 154(b) by 184 days.

(21) Appl. No.: 14/949,158

(22) Filed: Nov. 23, 2015

(65) Prior Publication Data

US 2016/0074644 A1 Mar. 17, 2016

Related U.S. Application Data

(60) Division of application No. 11/251,488, filed on Oct. 14, 2005, now Pat. No. 9,192,749, which is a
(Continued)

(51) Int. Cl.
*A61M 37/00* (2006.01)
*A61B 5/15* (2006.01)
(Continued)

(52) U.S. Cl.
CPC ....... *A61M 37/0015* (2013.01); *A61B 5/1411* (2013.01); *A61B 5/14514* (2013.01);
(Continued)

(58) Field of Classification Search
CPC . A61B 17/205; A61B 5/1411; A61B 5/14514; A61M 2037/0023;
(Continued)

(56) References Cited

U.S. PATENT DOCUMENTS

| | | | | |
|---|---|---|---|---|
| 4,577,630 A | * | 3/1986 | Nitzsche | A61B 5/15186 606/182 |
| 6,197,040 B1 | * | 3/2001 | LeVaughn | A61B 5/150022 600/583 |

(Continued)

FOREIGN PATENT DOCUMENTS

| | | |
|---|---|---|
| WO | 00/44438 A1 | 8/2000 |
| WO | 02/030281 A1 | 4/2002 |

OTHER PUBLICATIONS

Exhibit A—List of the Documents Cited in U.S. Appl. No. 11/251,488.
(Continued)

*Primary Examiner* — Katherine M Shi
(74) *Attorney, Agent, or Firm* — Mayer Brown LLP

(57) ABSTRACT

An applicator device (10) is provided for applying a patch (44) having an array of microprotrusions (90) to the stratum corneum. The applicator device (10) includes a device body (12) and a piston moveable within the device body (12). A cap (16) is provided on the device body (12) for activating the device (10) to impact the stratum corneum with a microprotrusion array (44,90). The device (10) is capable of being cocked by one handed operation of the user which allows the device (10) to be used by patients having neither the strength nor the manual dexterity to cock other types of applicator devices.

10 Claims, 7 Drawing Sheets

Related U.S. Application Data continuation of application No. 09/976,763, filed on Oct. 12, 2001, now abandoned.

(60) Provisional application No. 60/240,436, filed on Oct. 13, 2000.

(51) Int. Cl.
    *A61B 5/145*      (2006.01)
    *A61B 5/151*      (2006.01)
    *A61B 17/20*      (2006.01)

(52) U.S. Cl.
CPC ...... *A61B 5/1519* (2013.01); *A61B 5/150022* (2013.01); *A61B 5/15113* (2013.01); *A61B 5/15117* (2013.01); *A61B 5/15142* (2013.01); *A61B 5/15194* (2013.01); *A61B 5/150259* (2013.01); *A61B 5/150282* (2013.01); *A61B 5/150824* (2013.01); *A61B 5/150984* (2013.01); *A61B 17/205* (2013.01); *A61M 2037/0023* (2013.01); *A61M 2037/0046* (2013.01); *A61M 2037/0061* (2013.01)

(58) Field of Classification Search
CPC ...... A61M 37/0015; A61M 2037/0046; A61M 5/1454; A61M 2005/202; A61M 2005/2026; A61M 2005/2013

USPC .... 606/167, 172, 181–186; 604/22, 46, 117, 604/118, 135, 272, 289, 506

See application file for complete search history.

(56) References Cited

U.S. PATENT DOCUMENTS

| | | | |
|---|---|---|---|
| 6,210,420 B1* | 4/2001 | Mauze | A61B 5/15186 606/181 |
| 6,258,112 B1* | 7/2001 | Schraga | A61B 5/150022 606/181 |
| 6,537,242 B1* | 3/2003 | Palmer | A61M 37/0015 600/309 |
| 2002/0022855 A1* | 2/2002 | Bobroff | A61M 5/158 606/185 |
| 2002/0130042 A1* | 9/2002 | Moerman | A61B 5/1486 204/403.01 |

OTHER PUBLICATIONS

Exhibit B—List of the Documents Cited in U.S. Appl. No. 09/976,763.
Henry et al.; "Microfabricated Microneedles: A Novel Approach to Transdermal Drug Delivery," Journal of Pharmaceutical Sciences; vol. 87, No. 8, Aug. 1998; pp. 922-925.
International Preliminary Examination Report of PCT/US01/31935 dated Aug. 7, 2002 (2 pages).

* cited by examiner

MICROBLADE ARRAY IMPACT APPLICATOR

This application is a divisional application of U.S. application Ser. No. 11/251,488, filed Oct. 14, 2005, which is a Continuation of U.S. application Ser. No. 09/976,763, filed Oct. 12, 2001, abandoned, which claims the benefit of U.S. Provisional Application Ser. No. 60/240,436, filed Oct. 13, 2000; the contents of each application are herein incorporated by reference in their entirety.

TECHNICAL FIELD

The invention relates to an apparatus and method for applying a penetrating member to the stratum corneum layer of the skin by impact, and more particularly, the invention relates to the use of an impact device to reproducibly penetrate the stratum comrneum with a penetrating member such as a microprotrusion array for transdermal delivery or sampling of an agent.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to their large size and molecular weight. In addition, polypeptides and proteins are easily degraded during and after penetration into the skin, prior to reaching target cells. Likewise, the passive transdermal flux of many low molecular weight compounds is too limited to be therapeutically effective.

One method of increasing the transdermal delivery of agents relies on pre-treating the skin with, or co-delivering with the beneficial agent, a skin permeation enhancer. A permeation enhancer substance, when applied to a body surface through which the agent is delivered, enhances the transdermal flux of the agent such as by increasing the permselectivity and/or permeability of the body surface, and/or reducing the degradation of the agent.

Another method of increasing the agent flux involves the application of an electric current across the body surface referred to as "electrotransport."

"Electrotransport" refers generally to the passage of a beneficial agent, e.g., a drug or drug precursor, through a body surface, such as skin, mucous membranes, nails, and the like. The transport of the agent is induced or enhanced by the application of an electrical potential, which results in the application of electric current, which delivers or enhances delivery of the agent. Electrotransport delivery generally increases agent delivery and reduces polypeptide degradation during transdermal delivery.

There also have been many attempts to mechanically penetrate or disrupt the skin in order to enhance the transdermal flux. See for example, U.S. Pat. No. 5,879,326 issue to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue U.S. Pat. No. 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365. These devices use piercing elements of various shapes and sizes to pierce the outermost layer (i.e., the stratum corneum) of the skin. The penetrating elements disclosed in these references generally extend perpendicularly from a thin, flat member, such as a pad or sheet. The penetrating elements in some of these devices are extremely small, some having dimensions (i.e., a microblade length and width) of only about 25-400 μm and a microblade thickness of only about 5-50 μm. Other penetrating elements are hollow needles having diameters of about 10 μm or less and lengths of about 50-100 μm. These tiny stratum corneum piercing/cutting elements are meant to make correspondingly small microslits/microcuts in the stratum corneum for enhanced transdermal agent delivery therethrough. In many instances, the microslits/microcuts in the stratum corneum have a length of less than 150 μm and a width which is substantially smaller than their length.

Skin penetrating devices are used to penetrate the outermost layer of the skin, i.e., stratum corneum, with a plurality of microprotrusions to form pathways through which an agent such as a drug can be introduced, i.e., delivered, or an agent such as a body analyte can be withdrawn, i.e., sampled. The perforated skin provides improved flux for sustained agent delivery or sampling through the skin.

When microprotrusion arrays are used to improve delivery or sampling of agents through the skin, consistent, complete, and repeatable penetration is desired. Manual application of a skin patch having microprotrusions protruding from its skin-contacting side often results in significant variation in puncture depth across the length and width of the patch. In addition, manual application results in large variations in puncture depth between applications due to the manner in which the user applies the array. Accordingly, it would be desirable to be able to apply a microprotrusion array to the stratum corneum with an automatic device, which provides in a consistent and repeatable manner, stratum corneum piercing not only over the length and width of the microprotrusion array but also from application of one microprotrusion array to the next.

Some known spring loaded applicator devices for delivery of lancets for body fluid (e.g., blood) sampling are described in WO 99/26539 and WO 97/42886. However, these devices are difficult to use because they require two handed cocking of the applicator device prior to application. In particular, the known spring loaded lancet applicators require either two sections of the device to be pulled apart for cocking or require one part of the device to be twisted with respect to another part of the device for cocking. In both of these motions two handed cocking operation is required. Many of the patients using these devices possess neither the strength nor the manual dexterity to cock these known applicator devices.

Accordingly, it would be desirable to provide a spring loaded applicator for a skin penetrating member which is cocked by one handed operation of the user and which requires a minimal hand strength for cocking.

DISCLOSURE OF THE INVENTION

The present invention relates to an applicator for applying a penetrating member to the stratum corneum with impact. The penetrating member may be a microprotrusion array which is used to improve transport of an agent across the skin. The applicator includes a cocking mechanism which allows one handed cocking operation. The cocking mechanism requires minimal hand strength and dexterity since the cocking force can be applied by a user's arm.

In accordance with one aspect of the present invention, a device for impacting a penetrating member against the stratum corneum includes a device body for application of a penetrating member to the stratum corneum, a piston mounted within the device body for impacting the penetrating member against the stratum corneum, an impact spring between the piston and the device body for providing an impact force to the piston, and a cocking mechanism for cocking and locking the piston in a cocked position by compressing the device body and piston together using a compressing force which can be easily performed with one hand.

In accordance with an additional aspect of the present invention, a device for impacting a microblade array against the stratum corneum includes a device body, a piston mounted within the device body, the piston having a microblade array applying surface, an impact spring acting between the device body and the piston to impact the stratum corneum with the microblade array, a cap movably mounted on the device body, a hold down spring acting between the device body and the cap, a cocking mechanism for cocking and locking the piston in a cocked position with one hand by compressing the device body and piston together, and a piston release for releasing the piston from the cocked position to impact the stratum corneum with the microblade array when the hold down spring is compressed.

In accordance with a further aspect of the invention, a method of cocking a device for impacting a penetrating member against the stratum corneum includes the steps of moving a piston to a cocked position with respect to a device body by compressing the piston and device body together with only one hand, and locking the piston in the cocked position with the one hand.

In accordance with an additional aspect of the invention, a method of impacting a penetrating member against the stratum corneum includes providing an impacting device having a device body, a piston, and an impact spring; cocking the impacting device using only one hand by moving the piston to a cocked position with respect to the device body and locking the piston in the cocked position; mounting a penetrating member on the piston; and releasing the piston to impact the penetrating member against the stratum corneum

BRIEF DESCRIPTION OF THE DRAWINGS

The invention will now be described in greater detail with reference to the preferred embodiments illustrated in the accompanying drawings, in which like elements bear like reference numerals, and wherein.

MODES FOR CARRYING OUT THE INVENTION

The applicator device of the present invention is used for repeatable impact application of an array of microprotrusions to the stratum corneum in conjunction with transdermal therapeutic agent (e.g., drug) delivery or transdermal body analyte (e.g., glucose) sampling. Although the applicator device 10 is described for use with a certain type of microprotrusion array, it should be understood that the applicator device may also be used with other types of stratum corneum micropenetrating members. The applicator device can be used by patients having neither the hand strength nor the manual dexterity to cock other types of spring-loaded applicator devices. Further, the applicator device can be cocked and released with one-handed operation which provides certain advantages, for example, allowing a patient to apply a drug delivering microprotrusion array for local therapy on a site on the patient's own arm.

Figure 1:
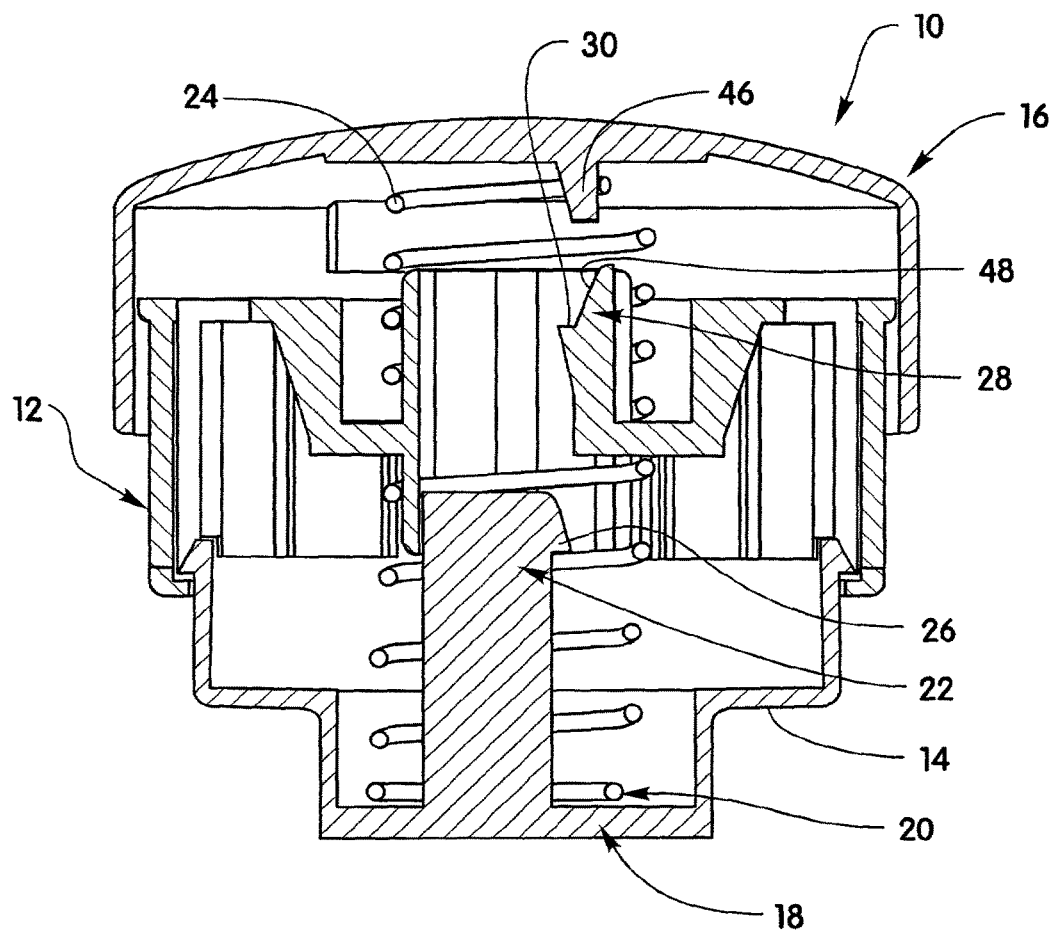
FIG. 1 is side cross sectional view of an applicator device in an initial configuration prior to cocking.

Turning now to the figures, FIG. 1 illustrates applicator device 10 including a device body 12 and a piston 14 movable within the device body. A cap 16 is provided on the device body 12 for activating the applicator to impact the stratum corneum with a microprotrusion array (not shown in FIG. 1). An impact spring 20 is positioned around a post 22 of the piston 14 and biases the piston downward with respect to the device body 12. The piston 14 has a lower surface 18 which is substantially planar, slightly convex, or configured to a body surface (i.e., a specific skin site). The lower surface 18 of the piston 14 causes a microprotrusion array or a transdermal patch containing a microprotrusion array to impact and pierce the stratum corneum.

Figure 2:
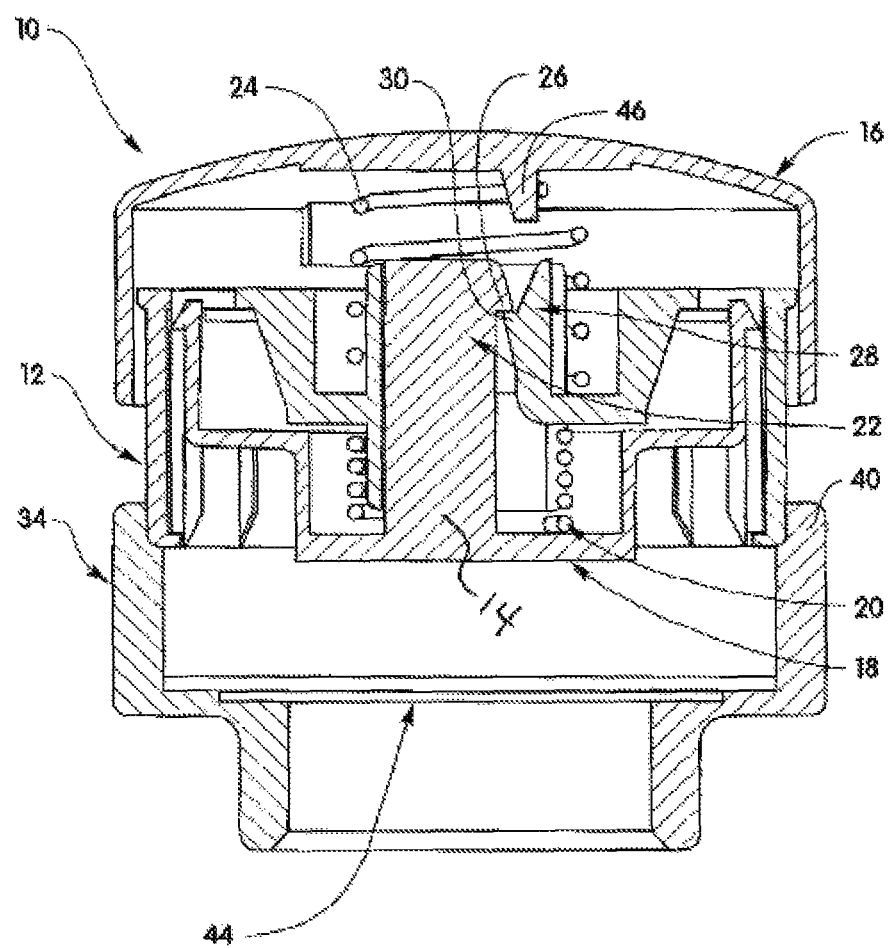
FIG. 2 is a side cross sectional view of the applicator device of FIG. 1 in a cocked position with a patch retainer attached to the applicator.

FIG. 1 shows the piston 14 in an uncocked position, while FIG. 2 shows the piston in the cocked position. When the applicator device 10 is cocked, the piston 14 is pressed up inside the device body 12 and locked in place by a locking mechanism. The locking mechanism includes a catch 26 on the post 22 and a flexible finger 28 on the device body 12 having a corresponding latch 30.

As the piston 14 is moved toward the device body 12 compressing the impact spring 20, the catch 26 flexes the finger 28 and snaps over the corresponding latch 30 of the flexible finger 28. The cocking step is performed by a single compression motion which both cocks and locks the piston 14 in the cocked position. This cocking step is easily performed with only one hand by compressing the applicator device 10 between a user's hand and another surface (e.g. a table top).

FIG. 2 illustrates the applicator device 10 with the piston 14 in a cocked configuration. As shown in FIG. 2, in the cocked position, the catch 26 and latch 30 on the piston 14 and device body 12 are releasably engaged preventing downward motion of the piston in the device body.

FIG. 2 also illustrates a patch retainer 34 mounted on the device body 12. The retainer 34 has an annular shape with a first end 40 which is configured to engage the device body 12. A second end 42 of the retainer 34 provides a stratum corneum contacting surface. A patch 44 is mounted between the first and second ends 40, 42 of the retainer 34. The patch 44 is suspended in the retainer 34. Although the manner in which the patch 44 is mounted in the retainer 34 and the location of the mounted patch 44 within the retainer 34 may vary (for example, the patch 44 may be positioned adjacent the second end 42 of the retainer 34) it is preferred to mount patch 44 recessed some distance from both ends 40 and 42 (as shown in FIG. 1) in order to avoid inadvertent contact of the patch microprotrusions with other objects (e.g., the fingers of the user).

According to one example, the patch 44 is connected by frangible sections of patch base material to an annular ring of patch material which is adhered to the retainer ring 34. The patch 44 is separated from the retainer ring 34 by the downward force of the piston 14. Alternatively, the patch may be releasably attached to the piston 14 or positioned on the skin beneath the piston.

The applicator device 10 can be used with a patch 44 which generally includes a microprotrusion array, an agent reservoir, and a backing. However, the applicator device 10 may also be used with a microprotrusion array without an agent reservoir. In this case, the microprotrusion array is used as a pretreatment which is followed by the application of an agent with a separate transdermal agent delivery or sampling device. Alternatively, the microprotrusion array may incorporate the agent as a coating on the microprotrusions, e.g. for delivering a vaccine intradermally. The application device 10 may also be used for impacting other micropiercing elements against the stratum corneum, for example those disclosed in Godshall et al, U.S. Pat. No. 5,879,326 and Zuck WO 99/29364, the disclosures of which are incorporated by reference herein.

In addition to being able to cock the device 10 with only one hand, device 10 is also designed to be operated (i.e., to cause release of the spring-loaded piston 14 and thus causing the patch 44 to impact the skin) using only one hand. The activation of the applicator device 10 by releasing the locking mechanism is performed by downward force applied to the applicator cap 16 while the second end 42 of the applicator device is held against the skin. The cap 16 is biased upwards by a hold down spring 24 which is positioned between the device body 12 and the cap. The cap 16 includes a pin 46 extending downward from the cap. When the cap 16 is pressed downward against the bias of the hold down spring 24, the pin 46 contacts a ramp 48 on the flexible finger 28 moving the flexible finger outward and disengaging the latch 30 of the flexible finger 28 from the catch 26. This releases the piston 14 and the piston moves downward impacting the stratum corneum with the patch 44.

Figure 3:
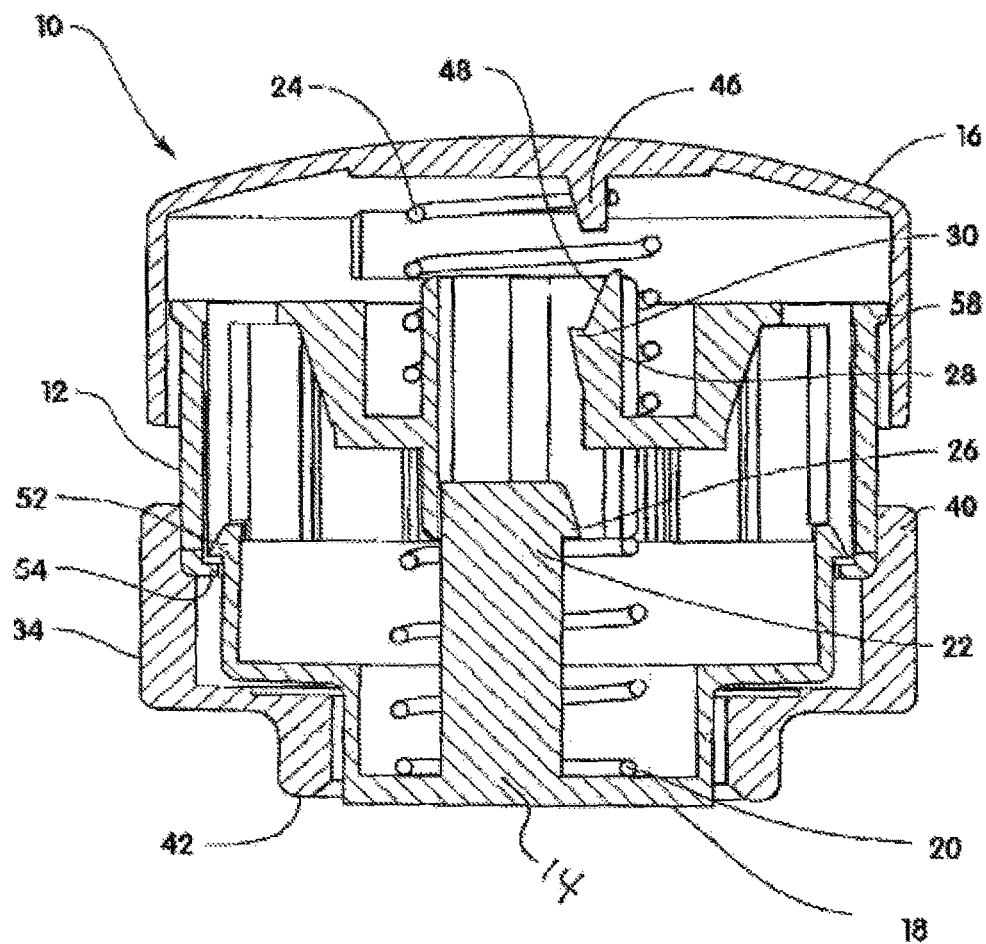
FIG. 3 is a side cross sectional view of the applicator device of FIG. 1 with the patch retainer of FIG. 2 after the piston has been released to apply the patch.

FIG. 3 illustrates the applicator device 10 after the device has been released and a patch has been applied to the stratum corneum. The hold down spring 24 is selected such that a predetermined hold down force must be achieved before the device is released. The hold down force causes the stratum corneum to be stretched by the second end 42 of the retainer 34 so that the skin is under optimal tension at the time the patch 44 impacts the skin. The hold down force applied by the hold down spring 24 is preferably selected to cause the second end 42 to apply a tension to the skin in the range of about 0.01 to 10 megapascals (MPa), more preferably about 0.05 to 2 MPa.

A balance between the hold down spring 24 and the impact spring 20 allows the cocking of the piston 14 by pressing on the cap 16 without causing the finger 46 to release the locking mechanism. The impact spring 20 is selected to achieve a predetermined impact which is appropriate for a particular patch to provide the desired penetration. The selection of the impact and hold down springs is described further in U.S. Provisional Patent Application Ser. No. 60/240,307 filed on even date herewith, which is incorporated herein by reference in its entirety.

The retainer 34 is attached to the device body 12 after cocking of the piston 14. The retainer 34 is attached by a snap in connection requiring less force to snap in than the force required to release the piston. The retainer 34 may also be attached to the device body by a bayonett fitting or a slide-on fitting which allows the retainer 34 to slide into the device body 12 in a direction normal to the axis of the applicator.

Figure 4:
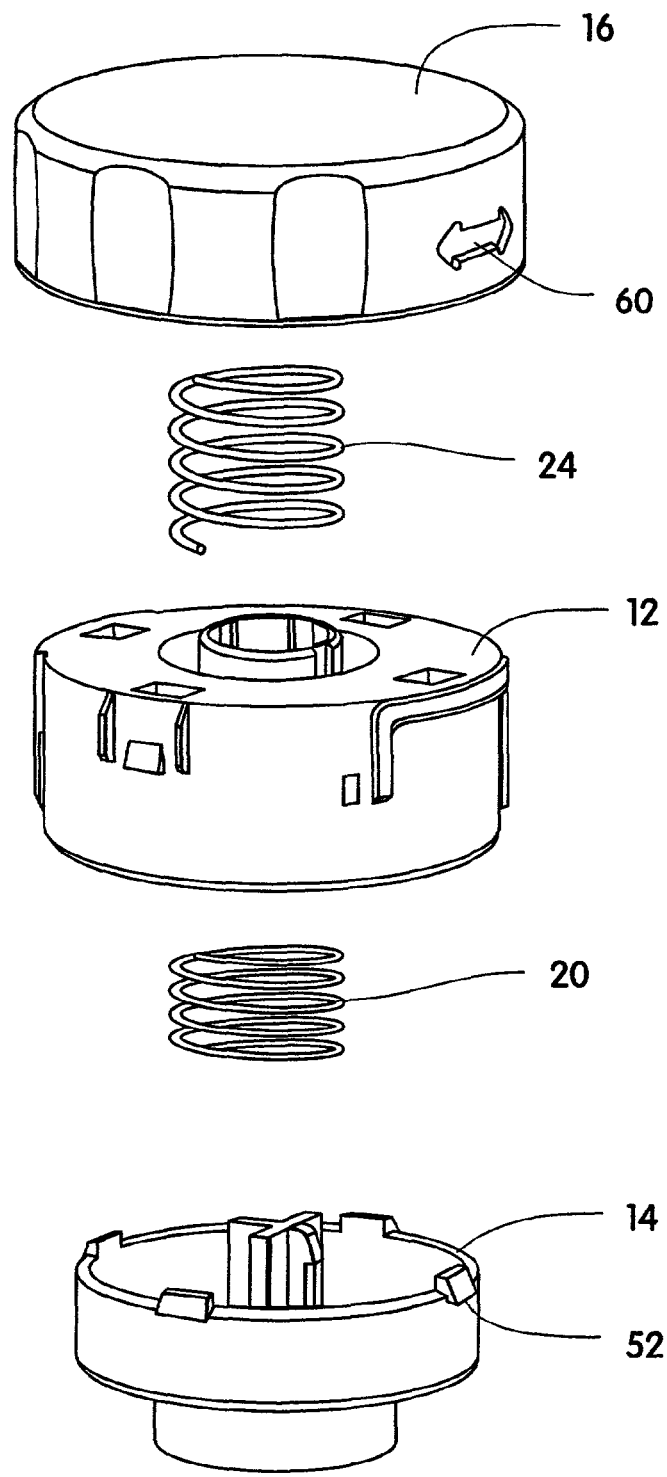
FIG. 4 is an exploded perspective view of the applicator device of FIG. 1.

FIG. 4 illustrates the cap 16, device body 12, and piston 14 in an exploded perspective view. As shown in FIG. 4, the piston 14 includes piston retainer tabs 52 which engage a lower rim 54 (FIG. 3) of the device body 12 and prevent the piston from being expelled from the device body. In addition, the cap 16 includes retainer tabs (not shown) which similarly engage an upper rim 58 (FIG. 3) of the device body 12 and prevent the cap from coming off of the body.

FIG. 4 also illustrates an optional rotational locking arrangement which allows the cap 16 to be rotated to a locked position at which activation of the applicator is not possible because the pin 46 is not aligned with the flexible finger 28. An indication of the locked or unlocked position of the cap 16 is provided through a window 60 in the cap. When the cap 16 is at positions other than the unlocked position, the pin 46 is not aligned with the ramp 48 on the flexible finger 28 and thus, the applicator cannot be released. While this optional locking feature prevents inadvertent activation of the applicator device 10, the relative rotational motion of the body 12 and the cap 16 generally requires the use of both hands, which in some cases is less desirable.

Figure 5:
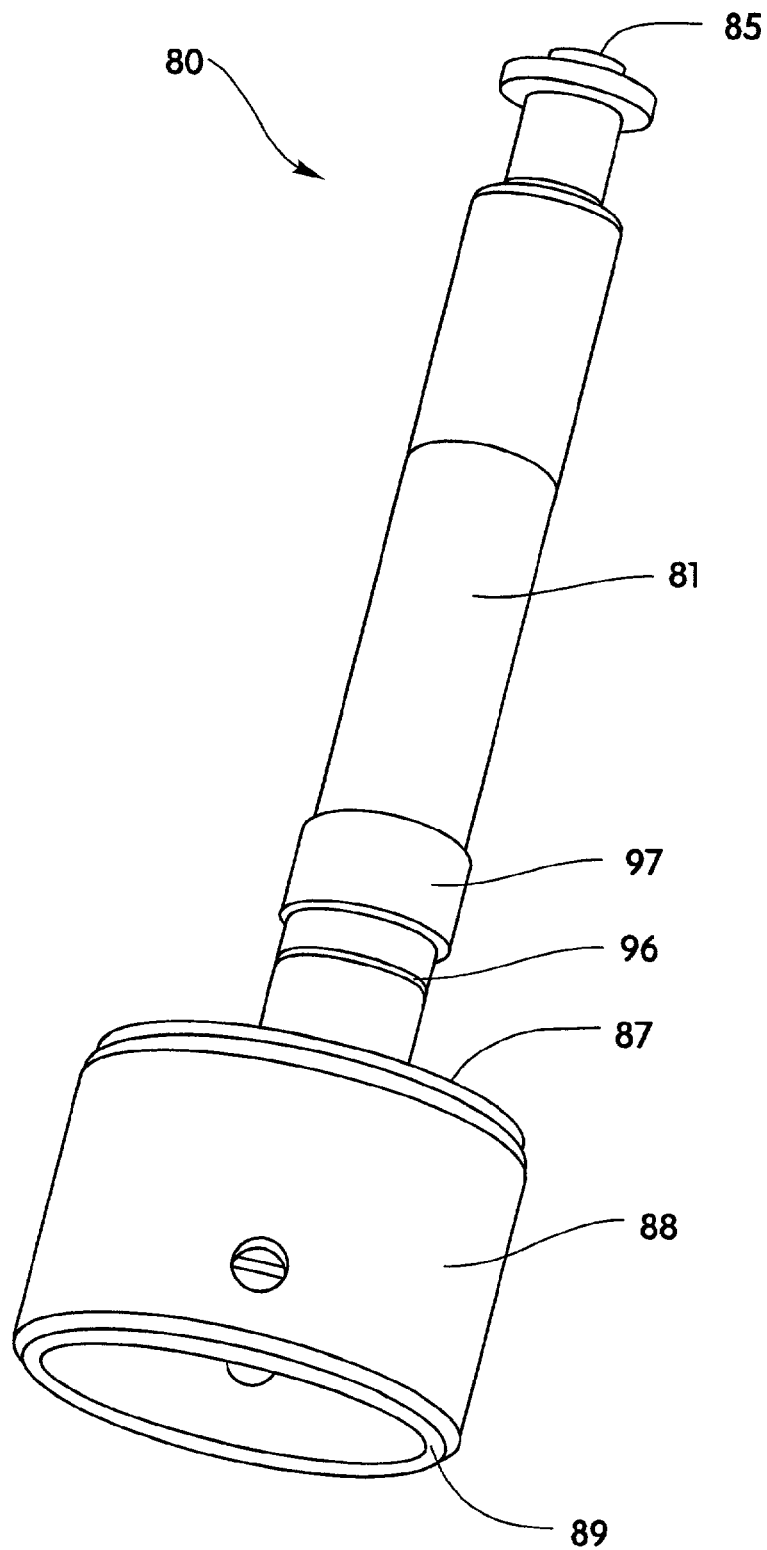
FIG. 5 is a perspective view of an alternative embodiment of an applicator device.
Figure 6:
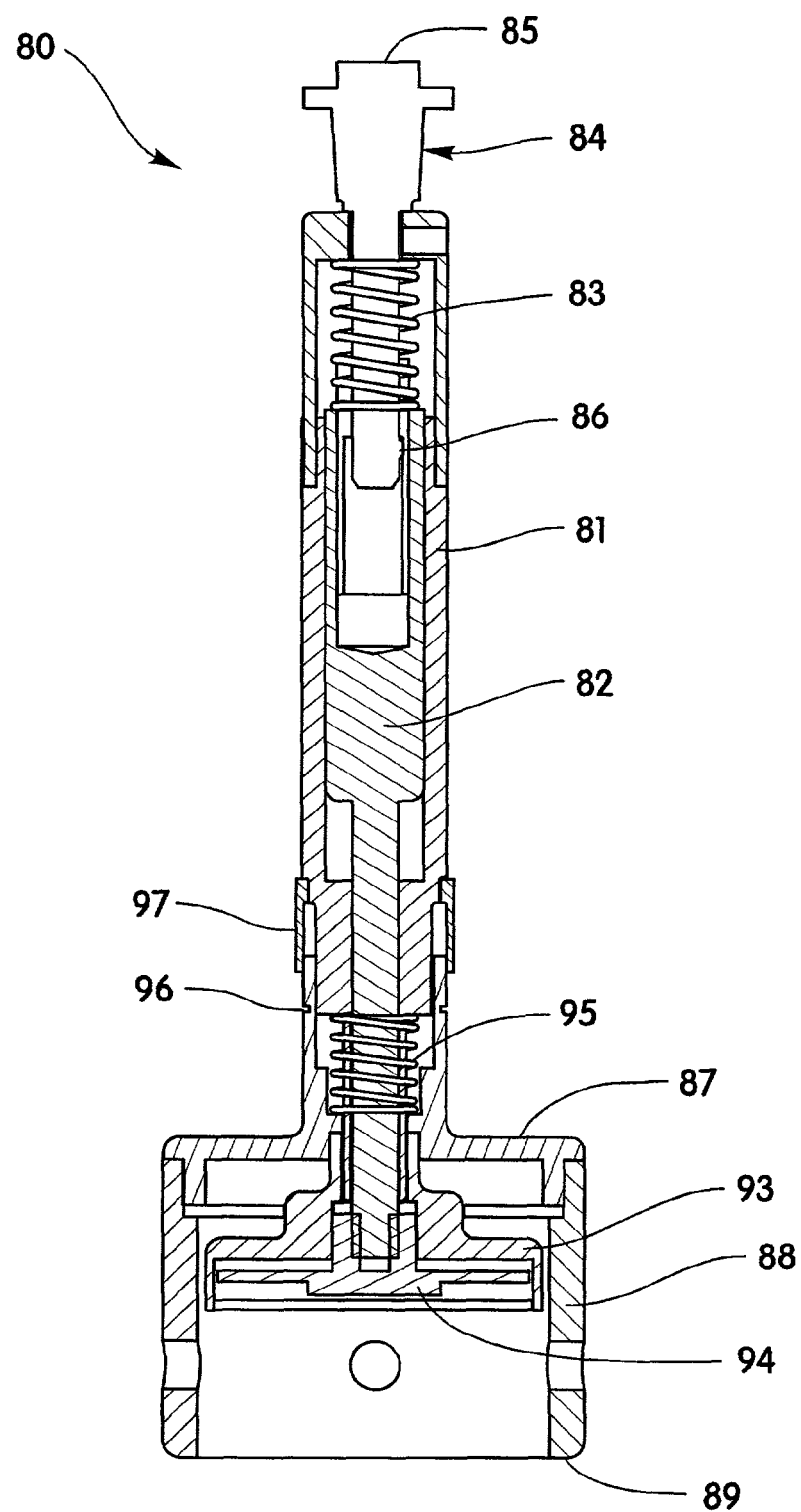
FIG. 6 is a side view, partially in section, of the applicator device of FIG. 5.

FIGS. 5 and 6 illustrate an alternative embodiment of an applicator 80 having a different shape and somewhat different cocking arrangement which also achieves the desired result of simple one handed cocking operation. According to this embodiment, the user grasps an outer cylinder 81 which acts as a handle for the device. A piston 82 is slidably engaged within the cylinder 81. An Impact spring 83, shown in compression in FIG. 6 biases the piston 82 away from the top or skin distal end of cyclinder 81. A releasable catch mechanism 84 (not shown in detail in FIG. 6) is provided whereby depression of button 85 causes latch 86 to retract thereby enabling compressed spring 83 to move piston 82 downwardly (i.e., in a direction towards the skin). Slidably engaging the skin proximal end of cyclinder 81 is a middle housing 87 having an indicator notch 96. Threaded to housing 87 is lower housing 88 which has a generally annular shape. A retainer 93, whose function is described in detail in U.S. Provisional Patent Application Ser. No. 60/240,379 filed on even date herewith and incorporated herein by reference is screwed onto the skin proximal end of cyclinder 81. Within retainer 93 is an impact head 94 which is attached to piston 82. Impact head 94 is adapted to hold, on its skin proximal surface, a patch having a plurality of microprotrusions (the patch is not shown in FIG. 6). A hold down spring 95, shown in compression in FIG. 6, is provided between cyclinder 81 and middle housing 87. Hold down spring 95 compresses when the user grabs cylinder 81, places edge 89 against the skin site to be pierced, and presses the device 80 against the skin site. As spring 95 is compressed, notch 96 becomes aligned with the lower edge of band 97. In this alignment, the hold down spring 95 is in a predetermined compression which provides the necessary hold down force and skin stretching at edge 89. Once the notch 96 is aligned with the lower edge of band 97, the operator simply presses button 85, which releases latch 86 which in turn releases piston 82 and head 94, causing head 94 to impact the microprotrusion member against the patient's skin.

The applicator devices 10 and 80, according to the present invention have been described with respect to an upright orientation in which the patch 44 is applied from a piston side of the device which is illustrated at the bottom/skin proximal end of the devices in the figures. It should be understood that the applicator devices may be used in other orientations (i.e., sideways and upside down) as long as the device is properly oriented against the skin site to be pierced.

Figure 7:
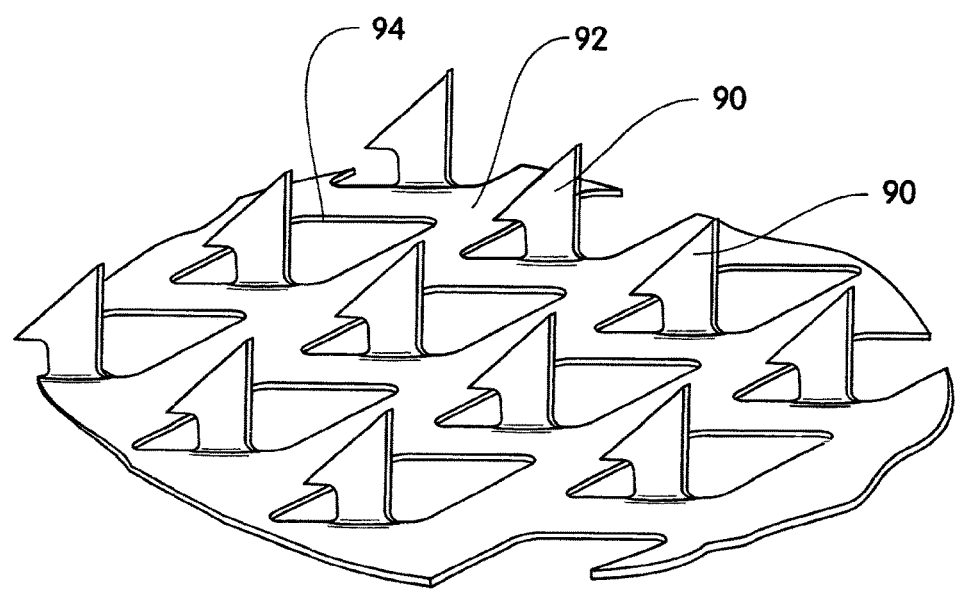
FIG. 7 is a perspective view of a portion of one example of a microprotrusion array.

FIG. 7 illustrates one embodiment of a stratum corneum penetrating member for use with the present invention. FIG. 7 shows a plurality of microprotrusions in the form of microblades 90. The microblades 90 extend at a substantially 90° angle from a metal sheet 92 having openings 94. The sheet 92 may be incorporated in an agent delivery patch or an agent sampling patch which includes an agent reservoir and an adhesive for adhering the patch to the stratum corneum. Examples of agent delivery and sampling patches which incorporate a microprotrusion array are found in WO 97/48440, WO 97/48441, WO 97/48442. The microprotrusion array of FIG. 7 without a reservoir may also be applied alone as a skin pretreatment.

The term "microprotrusion" as used herein refers to very tiny stratum corneum piercing elements typically having a length of less than 500 μm, and preferably less than 250 μm, which pierce through the stratum corneum into the underlying epidermis layer, or epidermis and dermis layers. However, the microprotrusions should not penetrate so deep into the dermis layer as to cause bleeding. In order to penetrate the stratum corneum, the microprotrusions preferably have a length of at least 10 μm, more preferably at least 50 μm. In general, microprotrusions penetrate the skin to a depth of no more than about 500 μm and preferably less than about 400 μm. The microprotrusions may be formed in different shapes, such as needles, hollow needles, blades, pins, punches, and combinations thereof.

The term "microprotrusion array" as used herein refers to a plurality of microprotrusions arranged in an array for piercing the stratum corneum. The microprotrusion array may be formed by cutting a plurality of blades from a thin metal sheet and folding each of the blades out of the plane of the sheet to form the configuration shown in FIG. 7. The microprotrusion array may also be formed in other known manners, such as by connecting multiple strips having microprotrusions along an edge of each of the strips. The microprotrusion array may include hollow needles which inject a liquid formulation.

Examples of microprotrusion arrays are described in U.S. Pat. No. 5,879,326 issue to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue U.S. Pat. No. 25,637 Issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365, all of which are incorporated herein by reference in their entirety.

The device of the present invention can be used in connection with agent delivery, agent sampling, or both. In particular, the device of the present invention is used in connection with transdermal drug delivery, transdermal analyte (e.g., glucose) sampling, or both. Transdermal delivery devices for use with the present invention include, but are not limited to passive devices, osmotic devices, pressure-driven devices, and electrotransport devices. Transdermal sampling devices for use with the present invention include, but are not limited to, passive devices, negative pressure driven devices, osmotic devices, and reverse electrotransport devices. The transdermal devices of the present invention may be used in combination with other methods of increasing agent flux, such as skin permeation enhancers.

The device of the present invention may be used with a microprotrusion array included in a transdermal delivery or sampling patch having adhesive for attaching the patch to the skin. Alternatively, the microprotrusion array and delivery or sampling patch may be two separate elements with the microprotrusion array used for pretreatment prior to application of the delivery or sampling patch.

While the invention has been described in detail with reference to the preferred embodiments thereof, it will be apparent to one skilled in the art that various changes and modifications can be made and equivalents employed, without departing from the present invention.

The invention claimed is:

1. A method of impacting a penetrating member against the stratum corneum, the method comprising: providing an impacting device having a device body, a piston, and an impact spring; cocking the impacting device using only one hand by moving the piston and the device body together to a cocked position whereby the piston is locked in the cocked position; providing a penetrating member; mounting said penetrating member on said impacting device; and releasing said piston to impact the penetrating member against the stratum corneum, wherein said penetrating member comprises microprotrusions and wherein the impacting device comprises a rotational locking arrangement.

2. The method of claim 1, wherein the releasing comprises: holding the impacting device against the stratum corneum with a predetermined hold down force.

3. The method of claim 1, wherein the microprotrusions are arranged in an array.

4. The method of claim 1, wherein the piston has a lower surface which is substantially planar, convex, or configured to a body surface.

5. A method of transdermal drug delivery, the method comprising: providing an impacting device having a device body, a piston, a penetrating member comprising a patch which includes microprotrusions, and an impact spring; cocking the impacting device using only one hand whereby the piston is locked in the cocked position; mounting said penetrating member on the device body; and releasing said piston to impact the penetrating member against the stratum corneum, wherein the impacting device is cocked by moving the piston and the device body together to a cocked position by compressing the impacting device between a user's hand and another surface.

6. The method of claim 5 wherein the patch is frangibly connected to a retainer, further, wherein the retainer is attached to the device body.

7. The method of claim 6, wherein the patch is separated from the retainer by the downward force of the piston.

8. The method of claim 7, wherein the patch comprises an adhesive for adhering the patch to the stratum corneum.

9. The method of claim 5, wherein the impacting device comprises a rotational locking arrangement.

10. The method of claim 5, wherein the piston has a lower surface which is substantially planar, convex, or configured to a body surface.

* * * * *